US012653918B2

(12) United States Patent (10) Patent No.: US 12,653,918 B2
Strassburger et al. (45) Date of Patent: Jun. 16, 2026

(54) WEARABLE FRAGRANCE DISPENSING DEVICES

(71) Applicants: Daniel J. Strassburger, Stamford, CT (US); Chris Ciaraldi, Stamford, CT (US)

(72) Inventors: Daniel J. Strassburger, Stamford, CT (US); Chris Ciaraldi, Stamford, CT (US)

( * ) Notice: Subject to any disclaimer, the term of this patent is extended or adjusted under 35 U.S.C. 154(b) by 558 days.

(21) Appl. No.: 18/712,429

(22) PCT Filed: Aug. 6, 2021

(86) PCT No.: PCT/US2021/044958
    § 371 (c)(1),
    (2) Date: May 22, 2024

(87) PCT Pub. No.: WO2022/032107
    PCT Pub. Date: Feb. 10, 2022

(65) Prior Publication Data
    US 2025/0001033 A1     Jan. 2, 2025

Related U.S. Application Data

(60) Provisional application No. 63/061,876, filed on Aug. 6, 2020.

(51) Int. Cl.
    *A61L 9/03*      (2006.01)
    *A44C 15/00*     (2006.01)
    (Continued)

(52) U.S. Cl.
    CPC ................ *A61L 9/03* (2013.01); *A45D 34/02* (2013.01); *A44C 15/002* (2013.01);
    (Continued)

(58) Field of Classification Search
    CPC .. A45D 34/02; A45D 34/00; A45D 2034/007; A61L 9/03; A61L 2209/11;
    (Continued)

(56) References Cited

U.S. PATENT DOCUMENTS 5,653,758 A * 8/1997 Daniels .................... A61L 27/50
                                                    623/23.72
2004/0161283 A1* 8/2004 Lithgow ................... A45F 3/14
                                                    401/48

(Continued)

OTHER PUBLICATIONS

International Search Report and Written Opinion of International Application No. PCT/US2021/044958 mailed Nov. 9, 2021, 7 pgs.

*Primary Examiner* — David J Walczak
(74) *Attorney, Agent, or Firm* — Lowenstein Sandler LLP

(57) ABSTRACT

A wearable fragrance dispensing device comprising a fragrance housing comprising a thermoplastic material and having at least one cavity for maintaining a liquid fragrance emitting composition, said fragrance housing having at least one port for said liquid fragrance emitting composition to egress said fragrance housing, and an input port for filling said at least one cavity with liquid fragrance emitting compositions, said input port comprising a one-way valve and an end section adapted to fit on the housing; wherein said dispensing device is incorporated into a wearable device; and wherein said wearable fragrance dispensing device passively emits said liquid fragrance emitting composition.

14 Claims, 12 Drawing Sheets

(51) Int. Cl.

| | | |
|---|---|---|
| *A45D 34/00* | (2006.01) | |
| *A45D 34/02* | (2006.01) | |
| *A61L 9/12* | (2006.01) | |

(52) U.S. Cl.
CPC ........... *A45D 2034/007* (2013.01); *A61L 9/12* (2013.01); *A61L 2209/11* (2013.01); *A61L 2209/134* (2013.01); *A61L 2209/15* (2013.01)

(58) Field of Classification Search
CPC ........... A61L 2209/134; A61L 2209/15; A61L 9/037; A61L 9/12; A44C 15/002
USPC ...... 222/146.2, 78; 239/34, 36, 211; 63/1.15
See application file for complete search history.

(56) References Cited

U.S. PATENT DOCUMENTS

| | | | | |
|---|---|---|---|---|
| 2008/0142624 | A1 | 6/2008 | Ivri et al. | |
| 2010/0155414 | A1 | 6/2010 | Hu | |
| 2016/0271287 | A1 | 9/2016 | D'Amico | |
| 2016/0310625 | A1* | 10/2016 | Hudson | A61L 9/127 |
| 2017/0216519 | A1 | 8/2017 | Vouillamoz et al. | |
| 2018/0373272 | A1* | 12/2018 | Kihm | B64U 30/24 |
| 2021/0337941 | A1* | 11/2021 | Nakamura | A44C 15/002 |
| 2023/0404224 | A1* | 12/2023 | Rodriguez-Sdassi | |
| | | | | B05B 15/62 |

* cited by examiner

10

10

100

100

100

WEARABLE FRAGRANCE DISPENSING DEVICES

CROSS-REFERENCE TO RELATED APPLICATIONS

This application claims priority to co-pending U.S. Provisional Application No. 63/061,876, filed on 6 Aug. 2020, which is incorporated herein by reference as if set forth in full.

FIELD OF THE INVENTION

The present invention generally relates to wearable devices and objects that provide either passive and/or active release of fragrance or pleasant smelling aromatics. More specifically this invention relates to various devices that may be readily worn by users and that house liquid or solid phase fragrance compounds, that through either an active or passive means release the fragrance or aromatic of the housed compound. In various embodiments, the devices may be configured as utility or ornamental wearable items, including by way of example, a tie-bar, tie pin, collar stay, lapel stay, button, eyeglasses, and/or jewelry such as earrings, necklaces, bracelets, cufflinks, rings, and different types of otherwise ornamental pins or pendants.

BACKGROUND OF THE INVENTION

The use by humans of fragrance or pleasant aromas, such as perfumes, colognes, and various eau de something, on or near their bodies, dates back thousands of years. Such usage typically has involved the placement of an oil or some other pleasant fragrance material on a wearer's skin or clothing and then allowing the fragrance to dissipate over time. One obvious limitation of such usage is that the wearer is limited to the particular fragrance applied, and then requiring to reapply the fragrance after the material or composition has dissipated. Another limitation is that given the aromatics of most colognes and perfumes, once applied, the fragrance continues to release until it is fully used or dissipated. More specifically, there is little to no user control of the fragrance release. Further, while there are certain compositions that are aromatic, but may cause irritations to some wearers if applied directly to the wearers skin.

The use of a wide variety of wearable devices that are capable of providing different outputs or measurements or uses for wearers of such devices has rapidly expanded as the miniaturization of components has advanced. Obvious examples include fitness trackers, smart watches, smart clothing or apparel, medical devices, and even wearable cameras. Each of these type of devices provides users, or those monitoring the wearers, such as in the medical context, with particular information such as heart rate, location (such as a global position system), rate of movement, and so on.

In view of the miniaturization of devices, objects, and components, wearables have also been considered and used to release a fragrance. Various devices and release mechanisms have been designed; however, none appear to be fully functional or effective.

One example of such a device is disclosed in U.S. patent application Ser. No. 14/337,685 for a System and Method for Emitting Fragrances, by Shah and assigned to Track-Mind Solutions, LLC (the "'685 application"). The '685 application discloses a method and apparatus "to determine a pattern of emitting scents uniquely tailored to a particular user, and to emit fragrances in response to environmental conditions." However, the '685 application does not provide any disclosure for a passive emission of any scents or a combined passive and active emission of any scents or fragrances.

Another example of a fragrance release device is shown in U.S. patent application Ser. No. 15/923,137 for a Wearable Fragrance Emission Device, also by Shah, and also assigned to TrackMind Solutions, LLC (the "'137 application"). The '137 application discloses a "wearable fragrance emission device [that] may store a fragrance emission pattern which correlates particular conditions with scents to be emitted from the device." Similar to the '685 application, the '137 application does not provide any disclosure or suggestion for a passive emission of any scents or a combined passive and active emission of any scents or fragrances.

In view of these and other devices and efforts to design an effective solution to the wearable fragrance desires and needs, and the fact there has not been widespread acceptance of any type of solution, there is still a need for an effective solution, device, and system that provides either passive and/or active user control of wearable fragrance emission. Accordingly, what is needed for users of various colognes, perfumes, and other aromatics is an effective wearable device that allows for user selected and user controlled release of a fragrance by an unobtrusive, and better still, ornamentally and aesthetically pleasing device. Such an apparatus or device does not appear to have been fully and specifically designed or disclosed within the relevant prior art.

SUMMARY OF DESCRIBED EMBODIMENTS

The present invention overcomes the disadvantages of the prior art and fulfills the needs described above by providing a wearable device that passively or actively releases a pleasant fragrance or aromatic.

A preferred aspect of the invention is a wearable fragrance dispensing device, comprising a fragrance housing having at least one cavity for maintaining a fragrance emitting composition, said fragrance housing having at least one port for said fragrance emitting composition to egress said fragrance housing, and an input port for refilling said at least one cavity with replacement fragrance emitting compositions, wherein said wearable fragrance dispensing device emits said fragrance emitting composition when said fragrance emitting composition is heated above approximately 33° C.

Another preferred embodiment of the invention is a similar wearable fragrance dispensing device, comprising a fragrance housing having at least one cavity for maintaining a fragrance emitting composition, said fragrance housing having at least one port for said fragrance emitting composition to egress said fragrance housing, and an input port for refilling said at least one cavity with replacement fragrance emitting compositions, but wherein said wearable fragrance dispensing device emits said fragrance emitting composition when said fragrance emitting composition is heated above approximately 25° C.

A further preferred aspect of the invention is a wearable fragrance dispensing device, comprising a fragrance housing having at least one cavity for maintaining a fragrance emitting composition, said fragrance housing having at least one port for said fragrance emitting composition to egress said fragrance housing, and an input port for refilling said at least one cavity with replacement fragrance emitting compositions, further comprising at least one heating element to increase temperature of said fragrance emitting composition when said heating element is activated; and a power source to power said heating element when said heating element is activated.

BRIEF DESCRIPTION OF THE DRAWINGS

For the purposes of illustrating the invention, the attached drawings show several aspects and embodiments that are presently preferred. However, it should be understood that the invention is not limited to the precise arrangement and configuration shown in the accompanying drawings.

DETAILED DESCRIPTION OF CERTAIN PREFERRED EMBODIMENTS

Figure 1:
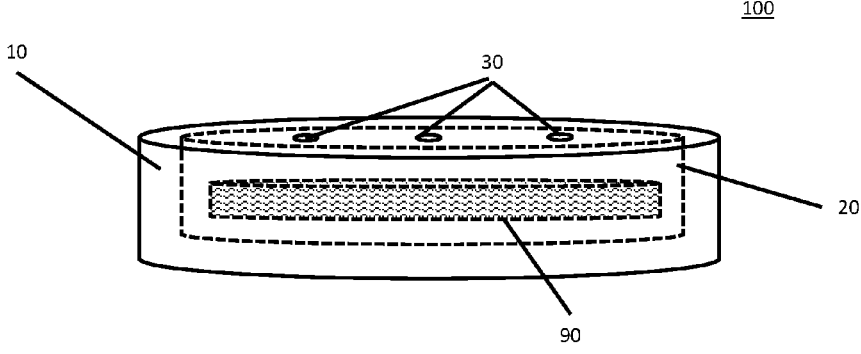
FIG. 1: is a side perspective cut-away view of an exemplary embodiment of the inventive wearable device fragrance dispenser.

The following provides a disclosure of different embodiments for wearable devices, including ornamental devices, such as jewelry, or utility devices, such as tie-bars or collar stays, that provide a passive and/or active means for dispensing or releasing one or more fragrances or aromatics.

This disclosure provides description of both passive and active releasing or dispensing of one or more fragrances or aromatics from various types of wearable devices. In certain embodiments, the wearable devices may be designed to include what are normally considered as utility and non-utility or ornamental embodiments, including by way of example, tie-bars, collar stays, lapel stays, cufflinks, buttons, as well as jewelry such as necklaces, earrings, bracelets, pins, and bracelets. Because the wearable device may be worn adjacent to, or touching the wearer's skin surface, when the wearable device is passively activated, the fragrance is dispensed as a function of increased temperature due to elevated skin temperature or body heat. In other actively controlled embodiments, the wearable device may be controlled by an active release mechanism that may include an electrical heating element with a power source that is able to controllably increase the temperature of the device, and thereby provide a controlled release of the fragrance or aromatic.

The core elements of the inventive wearable device 100 for releasing fragrance or aromatics, as shown in FIGS. 1 through 14, are a housing 10 defining a cavity 20 that maintains the fragrance emitting composition 90. The housing 10 further includes at least one fragrance emitting port 30, and one or more ports or openings 40 that provide a means for importing the fragrance emitting composition 90 into the housing 10 and specifically into the cavity 20. In a preferred embodiment, the ports or openings 40 could be configured as one-way ports or valves to ensure there is no leakage of the fragrance emitting composition once put into the housing 10.

Figure 2:
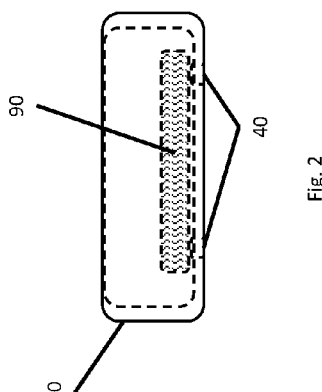
FIG. 2: is a side cut-away view of an exemplary embodiment of the inventive wearable device fragrance dispenser showing the input ports.
Figure 3:
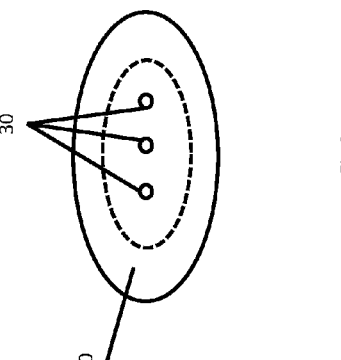
FIG. 3: is a top view of an exemplary embodiment of the inventive wearable device fragrance dispenser showing an embodiment of fragrance emitting ports.

As more specifically shown in FIGS. 1 through 3, in one embodiment, the wearable device 100 may have a plurality of fragrance emitting ports 30 where such ports are in vapor communication with the cavity 20 so that the fragrance from the fragrance emitting composition 90 is able to egress the cavity 20 when the fragrance emitting composition 90 is heated to a phase change where the fragrance emitting composition 90 begins a phase change to a vapor or gas and is thereby released through the fragrance emitting ports 30. Similarly, the wearable device 100 housing 10 may have one or more ports 40, as shown in FIG. 2 to allow for importing the fragrance emitting composition 90 into the housing cavity 20.

The fragrance emitting composition 90 may be a liquid, gel, or solid material, so long as the fragrance emitting composition 90 goes through a phase change at appropriate selected temperatures. In one embodiment, the fragrance emitting composition 90 would have a phase change at approximately 33° C. and above. Depending upon geography and locale, certain fragrance emitting compositions 90 may, for desired performance, have phase change characteristics at higher temperatures. For example, in hotter climates and locations, especially during summer months, fragrance emitting compositions 90 with phase change temperatures approximately equal to or higher than 40° C. may be preferably used. Similarly, in cooler or colder climates and locations, especially during the winter months, fragrance emitting compositions 90 having phase change temperatures approximately equal to or greater than 25° C. may be preferably used.

Figure 4:
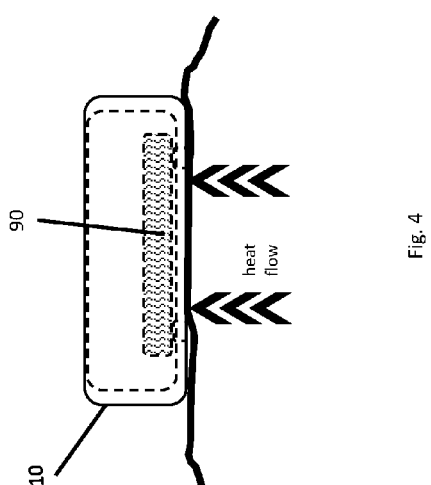
FIG. 4: is a side cut-away view of another exemplary embodiment of the inventive wearable device fragrance dispenser shown next a wearer's skin surface and showing heat flow from the wearer to the fragrance dispenser for passive heating.
Figures 4A, 4B:
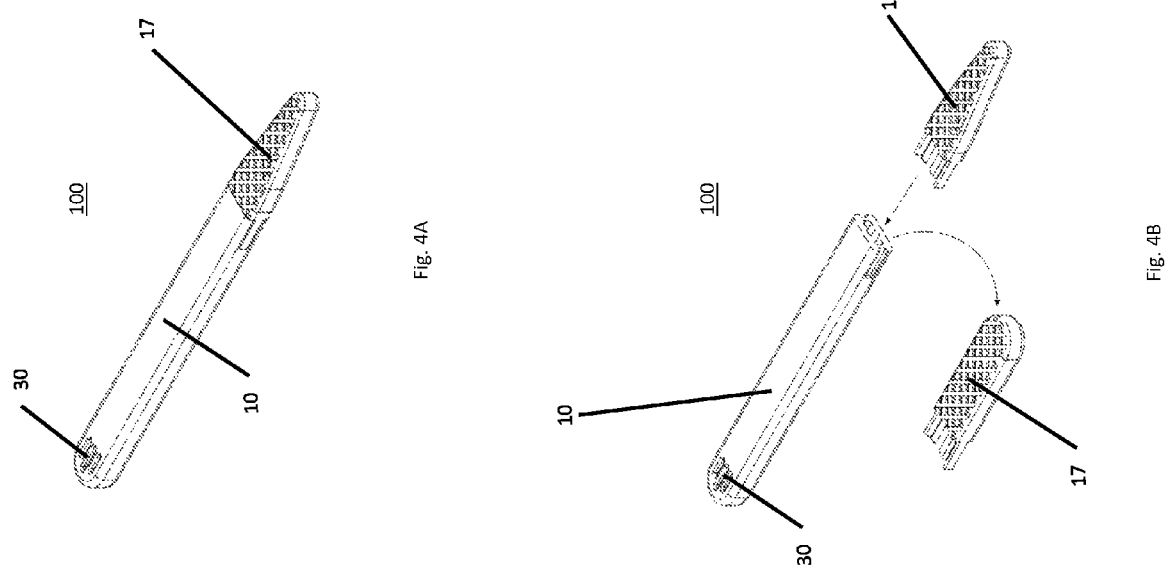
FIG. 4A: is a top perspective view of an exemplary embodiment of the inventive wearable device fragrance dispenser shown as a lapel or collar stay.
FIG. 4B: is a top perspective view of an exemplary embodiment of the inventive wearable device fragrance dispenser shown as a lapel or collar stay and showing interchangeable end sections.

In one passive embodiment, the wearable device 100 releases the fragrance from the fragrance emitting composition 90 through transmission of external (separate from the wearable device 100) heat, such as heat from the wearer's body, or heat from the local environment or outside air conditions. More specifically, the wearable device 100, and particularly, the housing 10 may be positioned on or closely adjacent to a wearer's skin, such that the wearer's body temperature increases the temperature of the wearable device 100, and specifically increases the temperature of the housing 10, as illustrated in FIG. 4. A further embodiment of the wearable device 100, where a liquid fragrance emitting composition 90 is used, could include a wick or similar liquid absorbing material within the cavity 20, to assist with a controlled release of the fragrance.

Given that for humans, the average outer skin temperature is approximately 33° C., by placing the wearable device 100 on, or next to the wearer's skin, the wearable device 100 and the housing 10 will be a heat sink and will result in an increased temperature of the housing 10, the wearable device 100, and the fragrance emitting composition 90. As the housing 10 temperature approaches 33° C., the fragrance emitting composition 90 will begin to undergo a phase change such that the fragrance emitting composition 90 will begin to emit the desired fragrance through the fragrance emitting ports 30.

In such a passive control embodiment, the placement or location of the wearable device would have a direct effect on the heat transfer and fragrance emission characteristics. For example, where the wearable device 100 is placed on known higher temperature body locations, such as behind a person's ears, or on a person's wrist, or around a wearer's lower neck area, then the fragrance emitting composition 90 is more likely to achieve a phase change to emit the desired fragrance. Similarly, if the wearable device 100 is place on a location that does not normally achieve higher temperatures, then the fragrance emitting composition 90 is less likely to emit the desired fragrance until the location where the wearable device 100 is positioned achieves a temperature approaching or reaching 33° C.

Figure 4C:
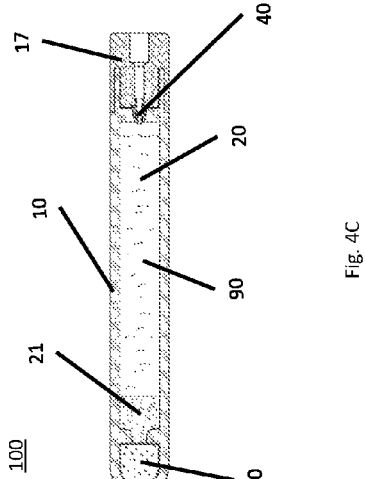
FIG. 4C: is a top cross-sectional view of an exemplary embodiment of the inventive wearable device fragrance dispenser shown as a lapel or collar stay.
Figure 4D:
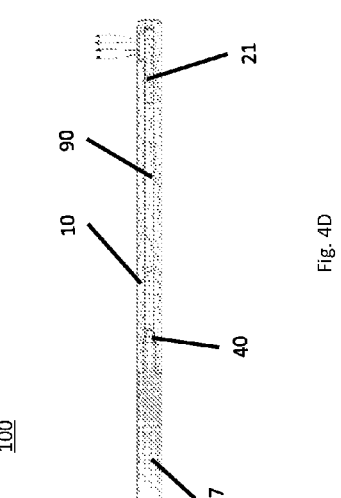
FIG. 4D: is a side cross-sectional view of an exemplary embodiment of the inventive wearable device fragrance dispenser shown as a lapel or collar stay.

FIGS. 4A through 4D show one type of embodiment of the wearable device 100 configured as a label or collar stay. In such a configuration and embodiment, the wearable device 100 may have interchangeable end section 17 to accommodate wearer needs for collar or lapel shape. As shown in FIGS. 4C and 4D, in such an embodiment, the wearable device 100 end that accepts the interchangeable end section 17, may also be the end with the input port 40, shown as a one-way valve, to allow for "charging" of the wearable device 100 with the fragrance emitting composition 90. As also shown in FIGS. 4C and 4D, the wick or liquid absorbing material 21 may be located between the cavity 20, housing the fragrance emitting composition 90, and the egress ports 30.

The housing 10 and/or other elements of the wearable device 100 may be fabricated using various thermoplastic materials including, without limitation, polypropylene, polyvinylchloride ("PVC"), low and high density polyethylene, polyethylene terephthalate, polystyrene, acrylonitrile butadiene styrene, polylactic acid, acetal polyoxymethylene, polyoxymethylene, polychlorotrifluoroethylene ("PCTFE"), and other similar thermoplastic materials and polymers, including by way of example, acrylic, polyester resin, nylon, and further including related co-polymers or combinations of thermoplastics, polymers, and resins exhibiting similar structural characteristics and properties.

Figure 5:
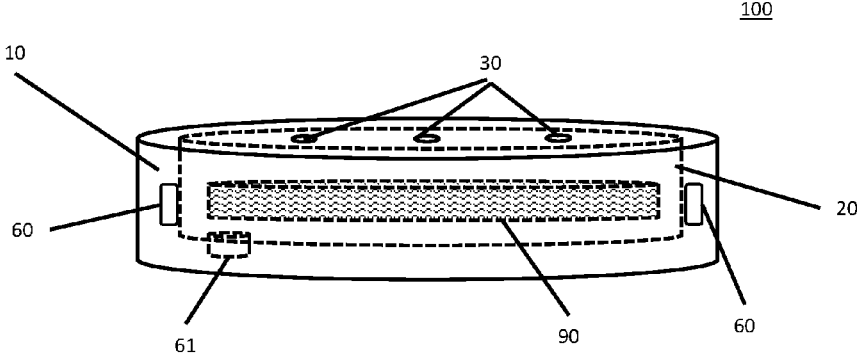
FIG. 5: is a perspective view of another exemplary embodiment of the inventive wearable device fragrance dispenser showing an exemplary implementation of heating elements.
Figure 6:
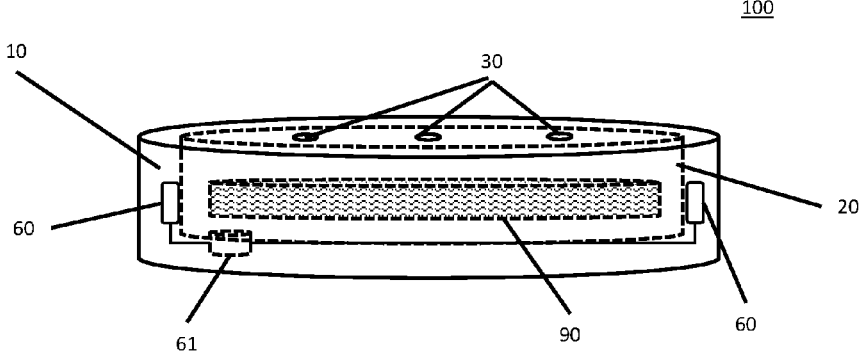
FIG. 6: is another side perspective view of an exemplary embodiment of the inventive wearable device fragrance dispenser with implementation of heating elements and a power source.

In an alternative embodiment, as shown in FIGS. 5 and 6, the wearable device 100 may include one or more active heating elements 60 embedded within or positioned next to the housing 10. The heating elements 60 may be one or more low power electrical resistors that are capable of controllably increasing the temperature of the housing. Such power output should preferably be less than 1 or 2 watts depending upon the size of the housing 10. The heating elements 60 should be electrically connected to one or more power sources or batteries 61. The power sources or batteries may be located within the housing 10 where the housing 10 size is able to accommodate a battery 61, or the batteries or power source 61 may be separate from the housing 10 so long as the power sources 61 are electrically connected to the heating elements 60 positioned in the housing 10.

Such a configuration with the power sources 61 being separate from the heating elements 60 and housing 10, may be readily implemented where the wearable device 10 allows for a separate power source to be stored or positioned in a pocket or other similar location that is proximate to the wearable device 100. One example of such an embodiment would be for a wearable device 100 being configured as a collar or lapel stay. In such a configuration, the power source 61 may be placed in the apparel pocket in close proximity to the collar or lapel stay.

For the active control wearable device 100, as described above, the heating elements 60, and accordingly the emission of fragrance may be controlled as a function of time by a clock or timer built into the wearable device. Such an embodiment may provide for the timed release and dispensing of a fragrance at, for example, 6:00 p.m., and provide for heating of the housing 10 for a set period of time, which may be for example, 5 minutes, 10 minutes, or longer periods of time.

Figure 7:
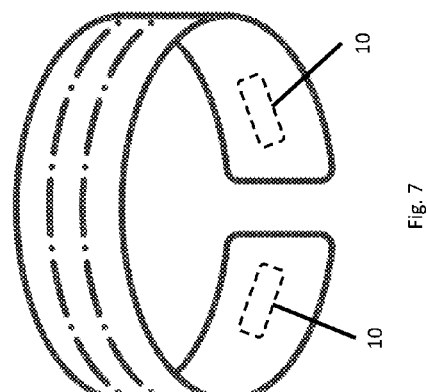
FIG. 7: is an exemplary embodiment of the inventive wearable device fragrance dispenser shown as a bracelet.
Figure 8:
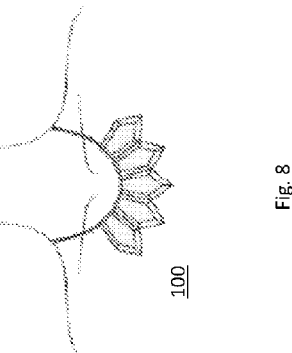
FIG. 8: is an exemplary embodiment of the inventive wearable device fragrance dispenser shown as a necklace.
Figures 9, 10:
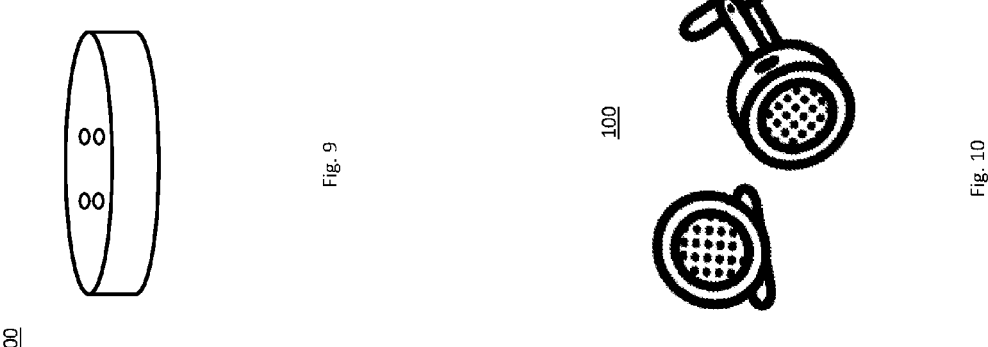
FIG. 9: is an exemplary embodiment of the inventive wearable device fragrance dispenser shown as a button.
FIG. 10: is an exemplary embodiment of the inventive wearable device fragrance dispenser shown as a set of cufflinks.

Although described and shown above as a generic housing and wearable device, the wearable device 100 and device housing 10, may be configured to be embedded within, or configured to be a wide variety of devices, including ornamental devices, or combined as a utility wearable device, possibly with an ornamental aspect. Several examples, as illustrated in FIGS. 7 and 8, include for ornamental devices, different examples of jewelry, which may be a bracelet, bracelet bobble, necklace, necklace bobble, or necklace pendant. In other embodiments not specifically shown, the wearable device 100 may be configured as a pin, pendant, one or more earrings, one or more ear cuffs, or one or more rings. Similarly, other examples and embodiments may be more utility in nature, as illustrated in FIGS. 9 through 10, as one or more cuff links, or one or more buttons used in various apparel. Other examples and embodiments, not specifically show, may include tie bars.

Figures 11, 12:
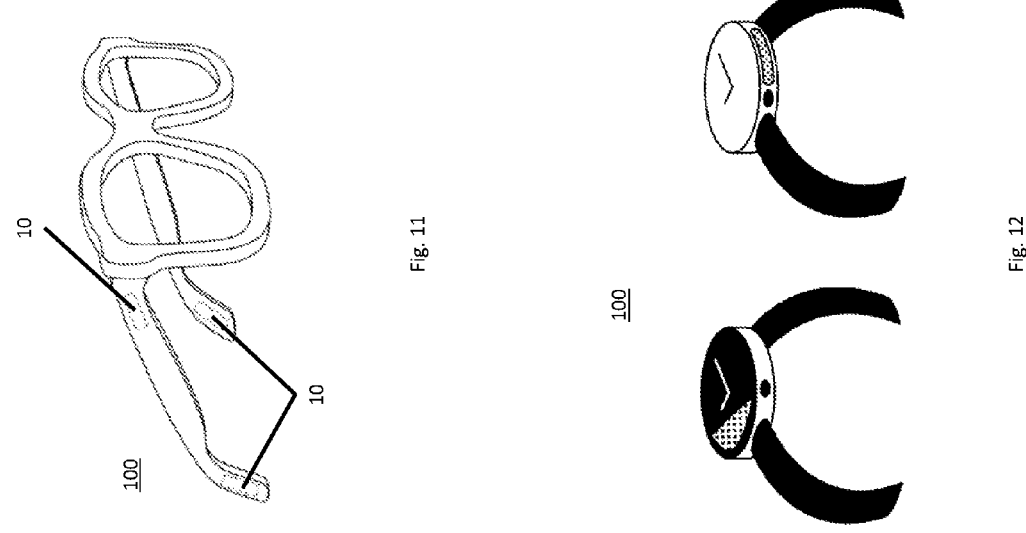
FIG. 11: is an exemplary embodiment of the inventive wearable device fragrance dispenser shown incorporated into eyeglass frame temple pieces.
FIG. 12: is an exemplary embodiment of the inventive wearable device fragrance dispenser shown incorporated into the face or body of a wrist watch.

In a further embodiment within the utility category, the housing 10 may be incorporated into the temple or arm sections of eyeglasses or sunglasses, as illustrated in FIG. 11. In such an eyeglass embodiment, the housing 10 may be embedded in the temple arm near the front section of the arm, or alternatively it may be positioned near the opposite end of the eyeglasses arm so that the housing 10 is positioned behind the wearer's ear. For such an embodiment, the location of the housing 10 and wearable device 100 near a wearer's temple or behind a wearer's ear, allows for passive controlled release of the fragrance emitting composition because those two body locations are known for having elevated skin surface temperatures.

Another embodiment, also within the utility category, is where the housing 10 is incorporated as part of a wristwatch, either included as part of the watch face or body, as shown in FIG. 12, or included within the watch wristband. With such an embodiment, and where the watch has an inherent timer, the watch may be used to actively control the wearable device 100 to release fragrance as set times during the day or night. As above for the eyeglasses embodiment, the watch wristband embodiment also allows for passive controlled release of the fragrance emitting composition because a human's wrist area, especially the underside of the wrist is known for having an elevated surface temperature because of the proximity of blood vessels near the skin surface.

Figure 13:
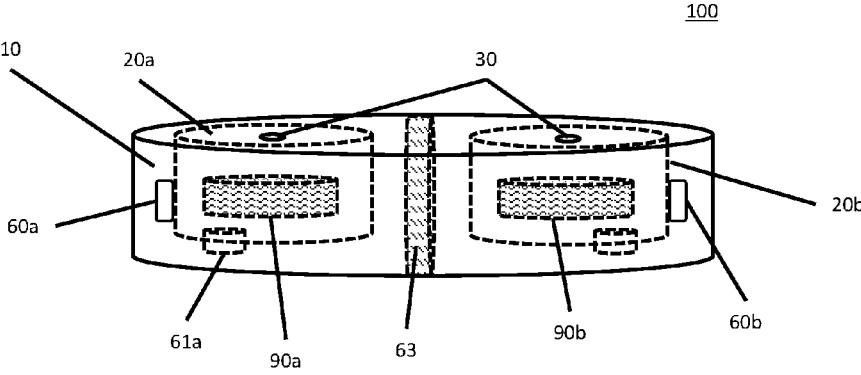
FIG. 13: is a side perspective view of an exemplary embodiment of the inventive wearable device fragrance dispenser showing an implementation with two separate composition cavities.

As shown in FIG. 13, in a different embodiment, the housing 10 may have more than a single cavity 20 so that different fragrance emitting compositions 90 may be housed and used with the wearable device 100. Such a multiple fragrance emitting composition 90 embodiment would be most applicable with an active control of the heating means. More particularly, with multiple cavities 20a and 20b, as shown in FIG. 13, and with multiple separate heating elements 60a and 60b, the wearer would be able to select which fragrance to release depending upon his or her desires. The multiple cavities 20a and 20b may contain separate fragrance emitting compositions 90a and 90b, respectively. The power source 61a may be electrically connected to the heating elements 60a and 60b. Such a configuration of the housing 10 should include insulating elements 63 to ensure thermal separation of the multiple cavities 20a and 20b, and thereby ensure only the release of the desired or selected fragrance.

Figure 14:
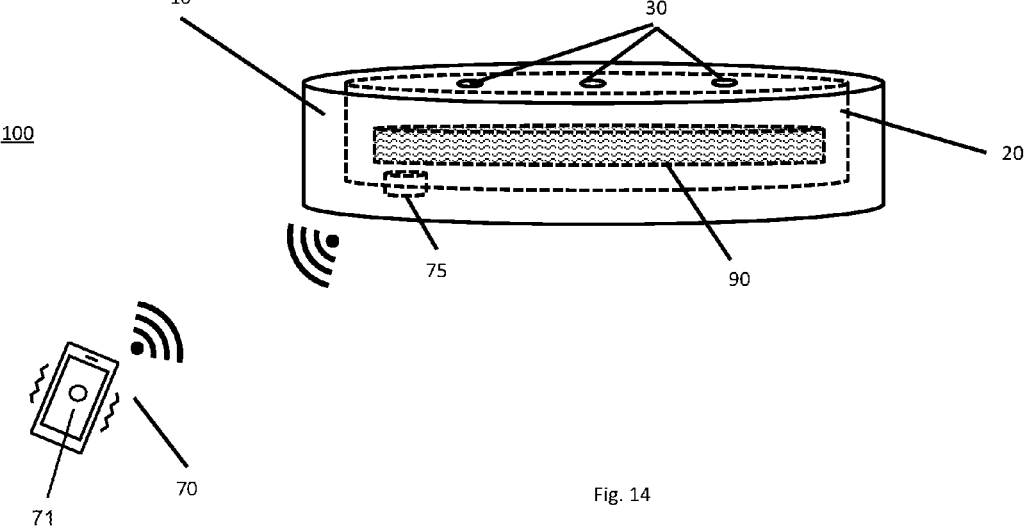
FIG. 14: is an illustration of an exemplary embodiment of the inventive wearable device fragrance dispenser showing implementation of near field communication and control by a smart device.

A further embodiment of the wearable device 100 having active control heating elements 60, and further having a data communication link or capability, may allow for remote or smart device control of the wearable device 100. As illustrated in FIG. 14, the wearable device 100 with a transceiver 75 may wirelessly receive and transmit data to a smart device 70 such as a smartphone, tablet, smartwatch, or other interface device. The smart device 70 would maintain, operate, and manage an app 71. Such a remote control configuration allows for many alternative embodiments for active control of the wearable device 100, and active control of the release of the fragrance emitting composition 90.

By way of example, the app 71 may be designed and configured to provide the user with the ability to control on-off status of the wearable device 100, where the on-off status may be a function of time of day, or with additional sensors and data input, the on-off status may be a function of other metrics. Such other control metrics may include heart rate, respiration, perspiration, body temperature, and other similar wearer sensed metrics. In one embodiment, the wearable device 100 and heating element 60 may be activated and controlled, and thereby release the fragrance emitting composition 90 as a function of elevated heart rate, respiration, perspiration, or body temperature. The app 71 may provide user selected thresholds such that if the wearer's heart rate exceeds 100 beats per minute, or respiration exceeds 20 breaths per minute, or increased perspiration or sweat.

In a further embodiment, that uses further wearer sensors, along with the data communication link with a remote smart device, and which in turn has a data connection to a global information network, such as the internet, additional analytics may be used to control the activation of the wearable device 100. By way of one example, and another embodiment, the wearable device 100 may include or be coupled to proximity sensors or aroma sensors. In such configurations, the wearable device 100 may be activated upon sensing of another person being proximate to the wearer. In such a configuration, the release of the fragrance emitting composition 90 may be a function of when another person is in close proximity to the wearer. With the app 71, certain metrics may be included such as the other person must be within 2 to 3 feet of the wearer, and must be within that zone of 2 to 3 feet for at least 10 seconds. Such an algorithm would prevent the activation of the device simply upon someone passing quickly by the wearer.

With respect to the aroma sensor, the sensing of outside aromas may allow for the wearable device 100 to not be activated. For example, if an aroma sensor coupled to the wearable device 100 senses another fragrance, for example from another person, then the wearable device 100 may shut off so as to not have conflicting fragrances. Similarly, an aroma sensor may be used to monitor the density of sillage of fragrance (e.g., how far the fragrance extends away from the source of the fragrance), such that if the sensor senses a level of fragrance above a certain threshold, then again, the wearable device 100 may shut off so as to not have an overpowering density of fragrance.

While preferred embodiments of the inventive apparatus and systems have been described and disclosed, in particular with reference to certain figures and exemplary embodiments illustrating and showing wearable devices that passively and actively release fragrance and aromatics, such exemplary wearable devices as described and illustrated are not to be construed as limiting the scope of application of the inventive apparatus and devices. For example, alternative wearables or means for wearing or using the housing, including within apparel, could be implemented with or as part of the disclosed wearable device 100, with each such alternative configurations providing additional utility of the device, and also maintain effectiveness of the apparatus as an aesthetically pleasing or concealed fragrance emitter.

It will be recognized by those skilled in the art that all such and other modifications, substitutions, and/or other applications are possible, and all such modifications, substitutions and applications are within the true scope and spirit of the present invention. It is likewise understood that the above disclosure and attached claims are intended to cover all such modifications, substitutions, and/or applications.

What is claimed is:

1. A wearable fragrance dispensing device, comprising:
a fragrance housing comprising a thermoplastic material and having at least one cavity for maintaining a liquid fragrance emitting composition, said fragrance housing having at least one port for said liquid fragrance emitting composition to egress said fragrance housing, and an input port for filling said at least one cavity with liquid fragrance emitting compositions, said input port comprising a one-way valve;
an interchangeable end section adapted to fit on the housing and removable to expose;
wherein said dispensing device is incorporated into a lapel stay wherein the end section when combined with the housing forms the shape of the lapel stay; and
wherein said wearable fragrance dispensing device passively emits said liquid fragrance emitting composition.

2. The wearable fragrance dispensing device, as described in claim 1, wherein the thermoplastic material is selected from the group consisting of polypropylene, polyvinylchloride ("PVC"), low density polyethylene, high density polyethylene, polyethylene terephthalate, polystyrene, acrylonitrile butadiene styrene, polylactic acid, acetal polyoxymethylene, polyoxymethylene, polychlorotrifluoroethylene ("PCTFE"), acrylic, polyester resin, nylon, co-polymers thereof and combinations thereof.

3. The wearable fragrance dispensing device, as described in claim 2, further comprising an attachment for attaching said wearable fragrance dispensing device to a lapel.

4. The wearable fragrance dispensing device, as described in claim 2, wherein said fragrance housing has multiple ports for said liquid fragrance emitting composition to egress said fragrance housing.

5. A method of passively emitting a liquid fragrance emitting composition, said method comprising:

(a) providing a wearable fragrance dispensing device comprising a fragrance housing comprising a thermoplastic material and having at least one cavity for maintaining a liquid fragrance emitting composition, said fragrance housing having at least one port for said liquid fragrance emitting composition to egress said fragrance housing, and an input port for filling said at least one cavity with liquid fragrance emitting compositions, said input port comprising a one- way valve, an interchangable end section adapted to fit on the housing, wherein said dispensing device is incorporated into a lapel stay wherein the end section when combined with the housing forms the shape of the lapel stay;

(b) removing the end section to expose the input port;

(c) filling said at least one cavity with liquid fragrance emitting composition through said one-way valve; and (d) returning said end piece to the end of the housing.

6. The method of passively emitting a liquid fragrance emitting composition, as described in claim 5, wherein the thermoplastic material is selected from the group consisting of polypropylene, polyvinylchloride ("PVC"), low density polyethylene, high density polyethylene, polyethylene terephthalate, polystyrene, acrylonitrile butadiene styrene, polylactic acid, acetal polyoxymethylene, polyoxymethylene, polychlorotrifluoroethylene ("PCTFE"), acrylic, polyester resin, nylon, co-polymers thereof and combinations thereof.

7. The method of passively emitting a liquid fragrance emitting composition, as described in claim 6, further comprising attaching said wearable fragrance dispensing device to a lapel.

8. The method of passively emitting a liquid fragrance emitting composition, as described in claim 6, wherein said fragrance emitting composition is a perfume.

9. The method of passively emitting a liquid fragrance emitting composition, as described in claim 6, wherein said fragrance emitting composition is a cologne.

10. The method of passively emitting a liquid fragrance emitting composition, as described in claim 6, wherein said fragrance housing has multiple ports for said liquid fragrance emitting composition to egress said fragrance housing.

11. The method of passively emitting a liquid fragrance emitting composition, as described in claim 5, further comprising the step of:

(d) after said liquid fragrance emitting composition has passively emitted for a period of time, refilling said at least one cavity with liquid fragrance emitting composition through said one-way valve.

12. The method of passively emitting a liquid fragrance emitting composition, as described in claim 11, wherein the thermoplastic material is selected from the group consisting of polypropylene, polyvinylchloride ("PVC"), low density polyethylene, high density polyethylene, polyethylene terephthalate, polystyrene, acrylonitrile butadiene styrene, polylactic acid, acetal polyoxymethylene, polyoxymethylene, polychlorotrifluoroethylene ("PCTFE"), acrylic, polyester resin, nylon, co-polymers thereof and combinations thereof.

13. A fragrance-emitting collar stay, comprising:

(a) a fragrance housing configured to accept an interchangeable end section, the housing comprising a thermoplastic material and having at least one cavity adapted to maintain a liquid fragrance emitting composition, the housing further comprising multiple ports for a fragrance to egress said housing;

(b) an end section accepted on the housing to form a collar stay, the end section removable to expose an input port wherein the end section when combined with the housing forms the shape of the collar stay;

(c) the import port including a one-way valve to add the liquid fragrance emitting composition.

14. A method of passively emitting a fragrance from a collar stay, the method comprising:

(a) disposing a fragrance housing configured to accept an interchangeable end section, the housing comprising a thermoplastic material and having at least one cavity adapted to maintain a liquid fragrance emitting composition, the housing comprising multiple ports for a fragrance to egress said housing, an input port comprising a one-way valve, and an end section disposed on the housing wherein the end section in combination with the housing forms the shape of the collar stay;

(b) removing the end section to expose the input port;

(c) filling the housing with liquid fragrance emitting composition through the input port;

(d) returning the end section to the housing; and (e) inserting the collar stay into a collar to allow fragrance to passively emit from the collar.

* * * * *